United States Patent [19]

Nguyen et al.

[11] Patent Number: 5,611,930
[45] Date of Patent: Mar. 18, 1997

[54] CELLULOSE ESTER BLEND MEMBRANES, PROCESS FOR MAKING SAME AND THEIR USE

[75] Inventors: Quang T. Nguyen, Ludres; Jean M. L. Néel, Villers-les-Nancy, both of France; Hartmut E. A. Brüschke, Nussloch; Hermann Steinhauser, Saarbrücken, both of Germany

[73] Assignee: Deutsche Carbone AG, Frankfurt, Germany

[21] Appl. No.: 135,403

[22] Filed: Oct. 13, 1993

[30] Foreign Application Priority Data

Oct. 13, 1992 [EP] European Pat. Off. .............. 92117467

[51] Int. Cl.$^6$ ................................................. B01D 61/36
[52] U.S. Cl. ...................................... 210/640; 210/500.3
[58] Field of Search ................................. 524/523, 560; 525/288; 210/640, 654, 655, 651, 500.29, 500.42, 500.32, 500.31, 500.3

[56] References Cited

U.S. PATENT DOCUMENTS

| | | | |
|---|---|---|---|
| 2,930,754 | 3/1960 | Stuckey | 210/500.29 |
| 3,847,822 | 11/1974 | Shuey | 210/500.28 |
| 4,774,365 | 9/1988 | Chen et al. | 568/697 |
| 4,824,528 | 4/1989 | Polak et al. | 204/427 |

*Primary Examiner*—Jeffrey T. Smith
*Attorney, Agent, or Firm*—Banner & Witcoff, Ltd.

[57] ABSTRACT

A method for removing $C_1$–$C_3$ alkanols from their mixtures with hydrocarbons or heteroatom-containing hydrocarbons wherein the method comprises utilizing a membrane comprising a non-porous separation layer of cellulose ester containing polymeric materials, characterized in that said polymeric material is a polymer blend of a first polymer selected from cellulose esters and at least one second polymer selected from polyvinyl pyrrolidone (PVP), copolymers of vinyl pyrrolidone and vinyl acetate (VP-co-VA), polyethylene glycol (PEG), N,N,-dialkylated polyacrylic amide (DPAA) and cellulose esters other than said first polymer.

9 Claims, No Drawings

CELLULOSE ESTER BLEND MEMBRANES, PROCESS FOR MAKING SAME AND THEIR USE

FIELD OF THE INVENTION

The present invention relates to cellulose ester blend membranes, a process for making same and their use for the removal of lower alcohols such as methanol and ethanol, from their mixtures with hydrocarbons, ethers, esters or ketones by pervaporation or vapor permeation processes.

BACKGROUND OF THE INVENTION

It is known that liquid mixtures can be separated into their components or that one component can be separated from a multicomponent liquid mixture by various methods. These methods include distillation, adsorption, extraction and other processes by which separation is effected through equilibrium distribution of components in different phases. It is also known that equilibrium processes for separation are subject to certain limitations. By distillation, for example, it is difficult to separate components with similar boiling temperatures or even impossible to separate azeotrope forming mixtures where complicated procedures requiring expensive equipment and causing high energy consumptions have to be used.

It is further known that liquid mixtures can be separated utilizing membrane systems and processes. Examples of such membrane processes are pervaporation or vapor permeation. In these processes the liquid mixture either in liquid form or as a saturated vapor is brought into contact with a first side (feed side) of a non-porous membrane. At least one component of the feed mixture shows a preferred permeatation through the membrane, as long as the partial vapor pressure of this component is lower at the second side (permeate side) of the membrane than at the feed side. The permeating vapor can be removed by condensation, continuous pumping, or a sweeping fluid. Various membranes are known useful for the separation of liquid mixtures in pervaporation processes, wherein the component to be separated from the mixture is generally that component which preferentially permeates the membrane.

EP-A-0 096 339, 0 307 636 and 0 442 557 as well as U.S. Pat. Nos. 4,802,988 and 4,892,661, for example, describe membranes useful for the separation of water from its mixtures with organic components, whereby the separating layer of the membrane comprises polyvinylalcohol. U.S. Pat. Nos. 4,670,146, 4,728,429 and 4,865,743 and EP-A-0 221 171 disclose ion-exchange membranes which also preferentially permeate water.

U.S. Pat. Nos. 4,590,098, 4,618,534 and 4,925,562 disclose so-called hydrophobic membranes which preferentially permeate organic components from their mixtures with water, preferably at low organic concentrations of the feed mixture. U.S. Pat. Nos. 5,039,422, 5,039,418, 5,039,417, 5,030,355, 5,019,666, 5,012,035, 4,944,880 and 4,802,987 and DE-A-2 627 629 disclose membranes useful for the separation of aromatic hydrocarbons from non-aromatic hydrocarbons.

U.S. Pat. No. 4,774,365 discloses an improved process for separation of excess methanol from ethers and $C_4$–$C_7$ raffinate in the production of methyltertiary-butylether (MTBE) and tertiaryamyl-methylether (TAME).

Examples of membranes found to be suitable for this operation are those of cellulose acetate, polyvinylalcohol, polysulfone, silicon rubber, and polysubstituted acetylenes, with the preferred membranes being cellulose acetate and polyvinylalcohol. Whereas some data are provided for the separation of methanol-MTBE and methanol MTBE-hexane (50:50 b.w.)-mixtures no further details of the cellulose acetate membranes used are given. U.S. Pat. No. 4,877,529 discloses a non-porous ion-exchange membrane comprising a perfluorinated acid resin having a side acid group, which has been contacted with a quarternary ammonium salt containing hydrocarbyl groups each having less than four carbon atoms. This membrane is described to be especially useful for the separation of methanol from MTBE containing low methanol concentrations.

U.S. Pat. No. 4,960,519 discloses a method for the removal of methanol from its mixtures with oxygenated compounds selected from organic ethers, aldehydes, ketones and esters. The membrane utilized comprises non-porous separating layers of a blend of polyvinylalcohol and polyacrylic acid on a polyacrylnitrile support layer.

STATEMENT OF THE INVENTION

In one aspect the invention relates to a membrane comprising a non-porous separation layer of a cellulose ester-containing polymeric material, wherein said polymeric material is a polymer blend of a first polymer selected from cellulose esters and at least one second polymer selected from polyvinylpyrrolidone (PVP), copolymers of vinylpyrrolidone and vinylacetate (VP-co-VA), polyethylene glycol (PEG), N,N-dialkylated polyacrylic amides (DPAA) and cellulose esters other than said first polymer.

In a further aspect the invention relates to a method of preparing a membrane comprising a non-porous separating layer as defined above characterized by (a) spreading a solution of said first and second polymers in an organic solvent on a dense carrier, slowly evaporating said solvent and removing the solvent-free membrane from said carrier, or (b) spreading a solution of said first and second polymers in an organic solvent on a dense carrier or on a woven or non-woven porous support, partially evaporating said solvent and then immersing the thus obtained precursor membrane in a water bath to obtain a skinned integral membrane as well as, optionally, removing said integral membrane from said carrier, or (c) spreading a solution of said first and second polymers in an organic solvent on a porous support membrane and slowly evaporating said solvent to obtain a composite membrane.

In yet a further aspect the invention relates to a process for removing $C_1$–$C_3$ alkanols from their mixtures with hydrocarbons or heteroatom-containing hydrocarbons, said method comprising contacting a feed mixture comprising at least one $C_1$–$C_3$-alkanol and at least one hydrocarbon or heteroatom-containing hydrocarbon in liquid phase or after evaporation with a first side (feed side) of a non-porous layer of a membrane, maintaining a gradient of a partial vapor pressure of the $C_1$–$C_3$-alkanol across said non-porous separating layer of said membrane, recovering from a second side (permeate side) of said membrane as a permeate a mixture richer in said $C_1$–$C_3$-alkanol and leaner in said hydrocarbon or heteroatom-containing hydrocarbon than the feed mixture, said permeate being recovered as a vapor at a pressure below the partial vapor pressure of said lower alcohol at the feed side, and recovering from the feed side of said membrane a product which is leaner in said $C_1$–$C_3$-alkanol and richer in said hydrocarbon or heteroatom, containing hydrocarbon, wherein the improvement comprises utilizing a membrane having a non-porous separating layer as defined above.

The latter process of the invention is especially advantageous if the $C_1$–$C_3$-alkanol forms an azeotropic mixture with the hydrocarbon or heteroatom-containing hydrocarbon, has a volatility similar to said hydrocarbons, and has to be removed without significant losses of said hydrocarbons.

DETAILED DESCRIPTION OF THE INVENTION

The non-porous separating layer of the membrane of the present invention consists of a polymeric material which is a polymer blend of a first polymer selected from cellulose esters and at least one second polymer selected from polyvinylpyrrolidone (PVP), copolymers of vinylpyrrolidone and vinylacetate (VP-co-VA), polyethylene glycol (PEG), N,N-dialkylated polyacrylic amides (DPAA), and cellulose esters other than the first polymer.

The first and second polymers are used in a weight ratio of from 90:10 to 10:90, preferably from 70:30 to 30:70 and most preferably from 60:40 to 40:60.

When the polymer blend contains VP-co-VA as second polymer, an even more preferred weight ratio is about 50:50.

With polymer blends containing a cellulose ester (other than the cellulose esters of the first polymer) as second polymer the weight ratio is generally from 90:10 to 10:90, preferably from 80:20 to 20:80 and most preferred from 70:30 to 30:70.

In a preferred embodiment the polymer blend used for the separating layer of the membrane is a ternary blend containing two different cellulose esters and polyethylene glycol (PEG) as third component which is contained in an amount from 10 to 50% b.w. based on the sum of the remaining two polymers.

The cellulose esters of the present invention include but are not limited to cellulose diacetate (CA); cellulose triacetate (CTA); cellulose acetate with an intermediate degree of acetylation between diacetate and triacetate, preferably with an acetyl content between 39 to 40% b.w.; cellulose nitrate (CN); cellulose propionate (CP); cellulose butyrate (CB); cellulose acetate-propionate (CAP) and cellulose acetate-butyrate (CAB).

Generally the copolymers of vinylpyrrolidone and vinylacetate (VP-co-VA) have a VP/VA mole ratio from 2:4 to 4:2, preferably from 2:3 to 3:2. The copolymer is preferred over the homopolymer PVP.

Polyethylene glycol (PEG) is a commercial product, available at different degrees of polymerization. Those fractions having average molecular weights in the range of 20 000 to 200 000, preferably around 50 000, are preferred. In a preferred embodiment the PEG is methylated at its end groups.

A preferred example of N,N-dialkylated polyacrylic amides is polyacrylopyrrolidide.

The cellulose esters and the other polymer blend components are soluble in a plurality of organic solvents such as acetone, cyclohexanone, dioxane, methylacetate, ethylacetate, formic acid, acetic acid, nitromethane, ethylene glycol ethers, chloroform or methylene chloride. The preferred solvents are acetone and dioxane or mixtures thereof, but other solvents or mixtures may be equally employed. The cellulose esters and the other blend components are added separately or combined to the stirred solvents or solvent mixtures, separate addition being preferred. Preferably, a further component is added only after complete dissolution of a former component. The solution is kept above or at room temperature (20° C.), preferably below room temperature. The concentration of the dissolved polymers can vary in a broad range, only limited by the maximum solubility. However, concentrations from 5 to 15% b.w., more specifically from 10 to 13% b.w., are preferred.

After complete dissolution of all components a viscous solution is obtained which may be filtered through a 5 to 100 µm filter in order to remove any undissolved matter.

Three different methods can be used for the preparation of membranes according to the present invention, as follows.

A) The solution of the polymer blend is spread on a glass plate or stainless steel plate preferably by means of a doctor blade. The solvent is slowly evaporated, to avoid any bubble formation, in dry air at room temperature (20° C.) or above room temperature (up to 50° C.). A typical evaporation time at 20° C. is from 2 to 5 hours. Especially when the evaporation takes place at room temperature, any moisture from the air has to be excluded. After evaporation of the solvent homogeneous films are obtained, which can be used as a membrane. The thickness of, such a film is in the range of 1 to 30 µm.

B) As in method A) the casting solution is spread on a glass or stainless steel plate or on a woven or non-woven porous fabric. The thickness of the polymer blend solution is generally from 10 to 800 µm with values from 70 to 200 µm being preferred. Only partial evaporation of the solvent is allowed with evaporation times typically between 5 to 60 seconds so as to generate on the surface a very thin non-porous skin, typically of about 0.1 to 1 µm thickness. After this evaporation time the precursor membrane is immersed in a water bath, preferably at temperatures from 0° to 20° C., whereby a so-called skinned integral asymmetric membrane is formed. After precipitation of the polymer blend (typically 1 to 60 min) the membrane is washed with water to remove excess solvents and dried. The total thickness of the membrane (without fabric) is typically from 5 to 100 µm.

C) By similar means as in methods A) and B) the polymer blend solution is spread on a porous support membrane, preferably an asymmetric ultrafiltration membrane. As in method A) the solvent is evaporated under mild conditions and exclusion of moist air, and a homogeneous film is obtained as a non-porous separating layer. The thickness of the polymer blend solution is adjusted in such a way that the final thickness of the dried non-porous separating layer is from 0.5 to 10 µm, preferably from 1 to 5 µm. The obtained membrane is a composite membrane.

The membranes of the present invention may be prepared according to method A, B or C in the form of flat sheets, with or without supporting or carrier layers. It is well understood, however, that other forms such as tubes, hollow fibers or the like may equally be produced.

The membranes of the invention are preferably used for the separation of $C_1$–$C_3$-alkanols from their mixtures with organic liquids by means of pervaporation, wherein the liquid mixture to be separated is fed to the feed side of the membrane in liquid phase or as vapor phase. For this reason, in addition to the term pervaporation the term vapor permeation is also used for this membrane separation method. The term pervaporation used throughout this specification is to be understood in this broad sense.

The $C_1$–$C_3$-alkanols include methanol, ethanol, propanol and isopropanol. These alkanoles are present in the starting mixture together with other organic compounds, preferably hydrocarbons or heteroatom-containing compounds, wherein the heteroatom is preferably oxygen. Examples are aliphatic hydrocarbons, such as hexane or heptane, aromatic hydrocarbons, such as benzene or toluene, and particular oxygen-containing compounds, such as ethers, aldehydes, ketones, esters and carboxylic acids. Of particular interest is the separation of said alkanols from mixtures which form azeotropes and are thus difficult to separate in accordance with other classical separation methods. A specific example is the separation of the corresponding alkanol with the preparation of ethyl tertiarybutyl ethers, for example the separation of methanol and ethanol with the preparation of methyl tertiarybutyl ether and ethyl tertiarybutyl ether.

When compared to the known membranes made from a cellulose ester alone, the polymer blend membranes of the present invention exhibit improved fluxes at virtually the same selectivities, or much better selectivities at similar fluxes.

The following examples illustrate the invention. All percentages are in weight-percent unless stated otherwise.

Example 1 (Comparison)

Solutions of cellulose diacetate (CA), cellulose triacetate (CTA), cellulose acetate-butyrate (CAB) and cellulose propionate (CP) in dioxane were prepared. The concentration of the respective cellulose ester in the solution was 10%. Following method A, each solution was spread on a glass plate, by means of a doctor blade, in a glove box through which dry nitrogen was passed. The solvent was allowed to evaporate, wherein the temperature of the dry nitrogen was increased to 40° C. during an evaporation period of 15 h. The thus formed non-porous films were peeled off from the glass plates and transferred to non-woven fabrics for better handling. The thickness of the non-porous cellulose ester films was between 4 and 20 µm. In pervaporation tests these cellulose ester films were tested with a feed mixture of 80% ethyltertiary butyl ether (ETBE) and 20% ethanol at 40° C. For better comparison all fluxes were calculated for a membrane thickness of 5 µm. The data obtained are shown in Table 1 and are used for comparing the improvement of fluxes and/or selectivities achieved with the membranes of the present invention.

TABLE 1

| Polymer | % | Flux (5 µm) kg/m² · h | EtOH % in permeate |
|---|---|---|---|
| CA | 100 | 0.08 | 99.9 |
| CTA | 100 | 0.15 | 99 |
| CAB | 100 | 0.92 | 95 |
| CP | 100 | 2.27 | 80 |

Example 2

A series of membranes was prepared, wherein a copolymer of vinylpyrrolidone (VP) and vinylacetate (VA) with a VP to VA mole ratio of 2 was blended into different cellulose esters. Mixtures of 20% acetone and 80% dioxane were used as solvents, the concentration of the dissolved matter as 10%. The non-porous films were prepared according to method A and tested as described in Example 1. Again fluxes were calculated for a thickness of 5 µm. The obtained results are summarized in Table 2.

TABLE 2

| Polymer | Ratio, % | Flux (5 µm) kg/m² · h | EtOH % in permeate |
|---|---|---|---|
| CA/VP-co-VA | 70:30 | 0.25 | 99.9 |
| CA/VP-co-VA | 60:40 | 0.45 | 99.9 |
| CTA/VP-co-VA | 50:50 | 1.03 | 99.2 |
| CTA/VP-co-VA | 70:30 | 0.4 | 98.5 |
| CTA/VP-co-VA | 60:40 | 0.61 | 99 |
| CTA/VP-co-VA | 55:45 | 0.75 | 98.5 |
| CTA/VP-co-VA | 40:60 | 1.6 | 98 |

A comparison of these data with those of Table I clearly shows the advantage of the polymer blend membranes over those of the single cellulose ester membranes. Blending of the VP/VA-copolymer into CA up to ratios of 50:50 improves fluxes up to a factor of 6, but does not change the excellent selectivities. The optimum blend ratios for CTA-copolymer blends are at 50:50. At higher ratios fluxes are lower, lower ratios lead to a decrease in selectivity.

Example 3

Solutions as prepared for Example 2 were used but the membranes were made according to method C spreading the cellulose ester blend solutions on an asymmetric polyacrylonitrile (PAN) ultrafiltration membrane, supported by a non-woven polyester fabric. The thickness of the non-porous separation layers thus obtained was between 2 and 5 µm. Test parameters were the same as in Example 1, the respective results are listed in Table 3.

TABLE 3

| Polymer | Ratio, % | Flux (5 µm) kg/m² · h | EtOH % in permeate |
|---|---|---|---|
| CA/VP-co-VA | 70:30 | 0.3 | 99.3 |
| CA/VP-co-VA | 50:50 | 1.15 | 98.7 |
| CTA/VP-co-VA | 60:40 | 0.72 | 98.9 |
| CTA/VP-co-VA | 50:50 | 1.2 | 99.1 |
| CAT/VP-co-VA | 40:60 | 1.75 | 98.2 |

The results thus obtained are in accordance with those of Example 2.

Example 4

In this example membranes were prepared according to method A, using blends of two cellulose esters. Test procedures were as described in Example 1.

TABLE 4

| Polymer | Ratio, % | Flux (5 µm) kg/m² · h | EtOH % in permeate |
|---|---|---|---|
| CA/CP | 70:30 | 0.2 | 99.6 |
| CA/CP | 30:70 | 1.9 | 84.6 |
| CAB/CN | 80:20 | 0.27 | 99.7 |
| CAB/CN | 90:10 | 0.57 | 98 |
| CTA/CN | 60:40 | 0.23 | 96 |

When comparing these results with those of Table 1 it follows that blending cellulose propionate (CP) into cellulose acetate (CA) at low concentrations (up to 30%)

improves flux without significant influence on selectivity. Higher ratios of CP/CA further improve fluxes but reduce selectivity to low values. The addition of cellulose nitrate (CN) to cellulose acetate butyrate (CAB) reduces flux but improves selectivity over that of pure CAB membranes, whereas blending of CN into CTA improves flux but reduces selectivity.

Example 5

To several binary cellulose ester blend solutions polyethylene glycol (PEG) of an average molecular weight of 20 000 was added. The membranes were produced according to method A and tested as described in Example 1. The results are listed in Table 5.

TABLE 5

| Polymer | Ratio, % | Flux (5 μm) kg/m² · h | EtOH % in permeate |
|---|---|---|---|
| CA/CN/PEG | 80:10:10 | 0.31 | 97.5 |
|  | 70:10:20 | 0.87 | 94.5 |
|  | 70:20:10 | 0.24 | 99 |
|  | 60:10:30 | 0.23 | 99.4 |
| CTA/CN/PEG | 70:10:20 | 0.4 | 97.5 |
|  | 60:10:30 | 0.2 | 99.4 |
| CAB/CN/PEG | 70:10:20 | 1.3 | 93 |
|  | 80:10:10 | 1.0 | 96 |

Compared to the data for the pure cellulose ester membranes (Table 1) and for the binary blends (Table 4) the addition of 10 to 50% PEG based on the sum of other polymers (11.1 to 43% PEG in Table 5) leads to a further improvement in flux while not significantly influencing selectivity.

Example 6

CA and CP membranes as prepared in Example 1 were tested with a feed mixture of 5% methanol in 95% n-heptane at 40° C. Fluxes and selectivities were compared with those obtained for binary cellulose ester blend membranes of Example 4 and cellulose ester-copolymer blend membranes of Example 2. The results are listed in Table 6.

TABLE 6

| Polymer | Ratio, % | Flux (5 μm) kg/m² · h | MeoH % in permeate |
|---|---|---|---|
| CA | 100 | 4 | 99.5 |
| CP | 100 | 6.5 | 97 |
| CA/CP | 70:30 | 4.9 | 99.2 |
| CA/VP-co-VA | 50:50 | 5 | 99.8 |

Similarily positive improvements of the blend membranes with respect to flux at nearly unchanged selectivity was found for the MeOH/n-heptane feed mixture.

Example 7

In a variation of Example 6, the CA/CP blend solution and the CA/VP-co-VA solution were spread on a glass plate and after an evaporation period of 30 s. immersed in water at 10° C. following method C. After washing and drying the obtained Skinned asymmetric membranes were peeled off, put on a non-woven polyester support and tested with the MeOH/n-heptane feed mixture. The overall thickness of these membranes was 90 μm whereas the thickness of the non-porous separation layer could not be determined. For this reason the data below cannot be directly compared with those shown in Table 6. However, the increased flux in Example 7 suggests a somewhat thinner membrane. For the CA/CP membrane a flux of 6.9 kg/m² h was measured at a methanol concentration of the permeate of 98.7%, the respective values for the CA/VP-co-VA membrane were 7.2 kg/m² h and 98.5% MeOH. This shows that with method C membranes with similarly good properties as with method A can be obtained.

Example 8

Membranes made according to method A of Example 1, Example 2 and Example 4 were used but tested with a feed mixture of 5% methanol in 95% methyltertiary butyl ether at 40° C. The results are listed in Table 7.

TABLE 7

| Polymer | Ratio, % | Flux (5 μm) kg/m² · h | MeoH % in permeate |
|---|---|---|---|
| CA | 100 | 0.07 | 99.2 |
| CAB | 100 | 2.55 | 87.5 |
| CA/CAB | 30:70 | 0.42 | 98.3 |
| CA/VP-co-VA | 60:40 | 0.4 | 99.9 |

The blend membranes show very good selectivity and improved flux compared to pure cellulose esters of comparable selectivity.

We claim:

1. A method for removing $C_1$–$C_3$ alkanols from their mixtures with hydrocarbons or heteroatom-containing hydrocarbons, said method comprising (a) contacting a feed mixture comprising at least one $C_1$–$C_3$-alkanol and at least one hydrocarbon or heteroatom-containing hydrocarbon in liquid phase or after evaporation with a first side (feed side) of a non-porous layer of a membrane, (b) maintaining a gradient of a partial vapor pressure of the $C_1$–$C_3$-alkanol across said non-porous separating layer of said membrane, (c) recovering from a second side (permeate side) of said membrane as a permeate a mixture richer in said $C_1$–$C_3$-alkanol and leaner in said hydrocarbon or heteroatom-containing hydrocarbon than the feed mixture, said permeate being recovered as a vapor at a pressure below the partial vapor pressure of said lower alcohol at the feed side, and (d) recovering from the feed side of said membrane a product which is leaner in said $C_1$–$C_3$-alkanol and richer in said hydrocarbon or heteroatom-containing hydrocarbon, wherein the improvement comprises utilizing a membrane comprising a non-porous separation layer of a cellulose ester-containing polymeric material, characterized in that said polymeric material is a polymer blend of a first polymer selected from cellulose esters and at least one second polymer selected from polyvinylpyrrolidone (PVP), copolymers of vinylpyrrolidone and vinylacetate (VP-co-VA), polyethylene glycol (PEG), N,N-dialkylated polyacrylic amides (DPAA) and cellulose esters other than said first polymer.

2. The method of claim 1, wherein said cellulose ester is selected from cellulose diacetate, cellulose triacetate, cellulose acetate butyrate, cellulose acetate propionate, cellulose propionate, cellulose butyrate and cellulose nitrate.

3. The method of claim 1 or 2, wherein said second polymer is a copolymer of vinylpyrrolidone and vinylacetate.

4. The method of claim 3, wherein said copolymer has a vinylpyrrolidone to vinylacetate ratio from 2:3 to 3:2.

5. The method of claim 1 or 2, wherein said first polymer and said second polymer are present in a weight ratio of from 70:30 to 30:70.

6. The method of claim 1 or 2, wherein said first and second polymers are present in a weight ratio of from 60:40 to 40:60.

7. The method of claim 3, wherein said first and second polymers are present in a weight ratio of about 50:50.

8. The method of claim 1 or 2, wherein said polymer blend is a ternary blend comprising two different cellulose esters and 10 to 50% by weight of a polyethylene glycol.

9. The method of claim 1 or 2, wherein said non-porous separating layer is a part of a skinned integral asymmetric membrane, or a layer of a composite membrane.

* * * * *